US006281014B1

(12) United States Patent
O'Brien et al.

(10) Patent No.: US 6,281,014 B1
(45) Date of Patent: Aug. 28, 2001

(54) SH3-CONTAINING PROTEIN, DNA AND USES THEREOF

(75) Inventors: Timothy J. O'Brien; Yinxiang Wang, both of Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/346,510

(22) Filed: Jul. 1, 1999

Related U.S. Application Data

(63) Continuation-in-part of application No. 08/871,732, filed on Jun. 9, 1997, now abandoned.
(51) Int. Cl.$^7$ .................................................. C12N 5/10
(52) U.S. Cl. ..................... 435/375; 530/300; 530/350; 530/358; 530/400
(58) Field of Search .................... 530/350, 358, 530/300, 400; 435/6, 7.21, 69.1, 91.1, 375; 536/23.1, 23.5, 24.1, 24.5; 424/139.1

(56) References Cited

PUBLICATIONS

Clarke, ND and Berg, JM., "Zinc fingers in C. elegans . . . ", Science 282, pp. 2018–2022, Dec. 1998.*

Desjarlais, J.R. et al., "Use of a zinc–finger consensus . . . ". PNAS (USA) vol. 90, p2256–2260, Mar. 1993.*

* cited by examiner

*Primary Examiner*—James Ketter
(74) *Attorney, Agent, or Firm*—Benjamin Aaron Adler

(57) ABSTRACT

The present invention encompasses an SH3 domain-containing TADG5 protein (SEQ ID No. 1), allelic variants or functional fragments thereof, a novel TADG5 DNA segment coding for the TADG5 protein (SEQ ID No. 2), allelic variants or functional fragments thereof, chimeric cells comprising the TADG5 DNA segment, expression vectors and plasmids comprising the TADG5 DNA segment and methods for producing the TADG5 protein. The present invention further encompasses methods of using the TADG5 protein (e.g., for gene regulation, etc.).

6 Claims, 17 Drawing Sheets

```
  1  gggcccccta ctaaagcctt ggggttagta cgcgtgcgca gcagtttctt
                                       ***
 51  ccgacagttg tgttgtgcca atggtggaga agaaaacttc ggttcgctcc
                           ---
101  caggaccccg ggcagcgggcg ggtgctggac cgggctgccc ggcagcgtcg
151  catcaaccgg cagctggagg ccctggagaa tgacaacttc caggatgacc
201  cccacgcggg actccctcag ctcggcaaga gactgcctca gtttgatgac
251  gatgcggaca ctggaaagaa aaagaagaaa acccgaggtg atcattttaa
301  acttcgcttc cgaaaaaact ttcaggcccct gttggaggag cagaacttga
351  gtgtgccga gggccctaac tacctgacgg cctgtgcggg acccccatcg
401  cggccccagc gccccttctg tgctgtctgt ggcttcccat ccccctacac
451  ctgtgtcagc tgcggtgccc ggtactgcac tgtgcgctgt ctggggaccc
501  accaggagac caggtgtctg aagtggactg tgtgagcctg ggcattccca
                                              ***
551  gagaggaagg gccgctgtgc actgcccggc cttcagaaag acagaatttc
601  atcacccaat gcaggggag catttcctcg tccaagggag agcctcactc
651  ctgggaactg tctggcaggt aggctgggcc ccccagtgct gttagattaa
                                                    •••••
701  aaatcctcgt gctggaaaaa aaaaaaaaaa aaaaa open reading frame (ORF) _____     initiation codon (Met)  ---
inframe stop codon upstream of ORF ★★★
inframe stop codon downstream of ORF ***
polyadenylation signal •••••                5' end of TADG5 →
```

Fig. 2

```
C-Fgr    alydy  eArt--Edd  LtftkG  ekfhiL  nnte-G  dwwearslssgkt
C-Tkl    alydy  epth--dgd  LglkqG  eklrvL  ees--G  ewwraQslttgqe
C-Abl    alydF  vAsg--dnt  LSitkG  eklrvL  gynhnG  ewceaQtk-ngq-
Ncf2a    vlfgF  vpetkEE--  LqvmpG  nivfvL  kk---G  ndnwatvmfngqk
Vav      aRydF  cArdrsE--  LslkEG  diikiL  nkk--G  qqgwwrgeiygrv
Tadg5    fRknF  qAll--EEqn LSvaEG  pn--yL  taca-G  ppsrpQrpfcavc
          *      **   **    *  *    *          *              *

C-Fgr    GciPSnY  vapVds
C-Tkl    GliPhnf  vamVns
C-Abl    GwvPSnY  itpVns
Ncf2a    GlvPcnY  lepVel
Vav      GwFPanY  veedys
Tadg5    G-FPSpY  tc-Vsc
          *   *
```

Fig. 6A

```
Tadg5   RKNFQALLEEQNLSVAEGP..NYLTACAGPPSRPQRPFCAVCGFPSPYT
        |:||  | :: .||:||     :| |  ::  :::::  ::  ||.|.|.
VAV     RYDFCA.RDRSELSLKEGDIIKILNKKGQQGWWRGEIYGRVGWFPANYV
```

Putative zinc finger:

1. AA 124-151 of Tadg5 is homologous to zinc finger II of TF III:
   (identities: 35%, positives: 57%)

```
              128 131        140  149
   Tadg5 124-SPYTCVSCGARYCTVRCLGTHQETRCLK-151
             +| ||  +| T|  +   +T+  |+T+|
   TFIII 104-NPYRCSQCGKAFRRTSDLSSHRRTQCIK-131
   ```

2. AA 111-133 of Tadg5 is homologous to zinc finger of a yeast protein:
   (identities: 47%, positives: 56%)

```
              117 120    128 131
   Tadg5 111-RPQRPFCAVCGFPSPYTCVSCGA-133
             ||| |+ T|+ T|+  T|||
         370-RPQDSYCPHCGYYQYVECVSCHA-392
   ```

3. AA 121-149 of Tadg5 is homologous to zinc finger of a yeast protein:
   (identities: 48%, positives: 65%)

```
              136    140  144   149
   Tadg5 121-GFPSPYTCVSCGARYCTVRCLGTHQETRC-149
             |+  +T|  +T|| +  T|+T  T|||T
         249-GYDSISSCVNCGNKICSVSCFKLHNETRC-277
   ```

Fig. 7

```
  19  cttcggttcgctcccaggacccccggcagcggctggtgctggaccgggct    68
         ||||||||||||||||||||||||||||||||||||||||||||||||||
  87  cttcggttcgctcccaggacccccgggcagcggcgggtgctggaccgggct   136

69  gcccggcgctgcgtcncatcaaccggcagctggaggccctggagaatgacta  118
         |||||||||||| ||||||||||||||||||||||||||||||||||||
 137  gcccggcagcgtcgcatcaaccggcagctggaggccctggagaatgacaa    186

119  ctttcaggatgactccca.tcggactccctcnnctcggcaagagactgc     167
         ||||||||||||||||| ||||||||||  ||||||||||||||||
 187  cttccaggatgaccccacgcgccccacgcgggactccctcagctcccctcagctcccctcagctcgggactcccctcagctcccc tcggcaagagactgc    236

168  ctcagtttgattactattcggacactggaaagaanagaanaataacc      217
         |||||||||||| |||||||||||||||||||| |:||| |:
 237  ctcagtttgatgacgatgcggacactggaaagaaaaagaaa....acc     283

218  cgaggtgatcattttaaacttcgcttccgaaaaactttcaggccctgtt    267
         ||||||||||||||||||||||||||||||||||||||||||||||||
 284  cgaggtgatcatttttaaacttcgcttccgaaaaactttcaggccctgtt   333
```

Fig. 9A

```
268  ggaggagcagaacttgagtgtgccgaggg.cctaactacctgacggcct  316
334  ggaggagcagaacttgagtgtgccgaggcccctaactacctgacggcct  383

317  gtgcgggacccccatcgcggccccagccgcctctctgtctctgtggc   366
384  gtgcgggacccccatcgcggccccagccgcccctctgtgtctctgtggc  433

367  ttcccatcccctacacctgtgtcagctgcgggtgccggtactgcactgt  416
434  ttcccatcccctacacctgtgtcagctgcgggtgccggtactgcactgt  483

417  gcgctgtctggggaccaccaggagaccaggtgtctgaagtggactgtgt  466
484  gcgctgtctggggaccaccaggagaccaggtgtctgaagtggactgtgt  533

467  gagcctgggcatt.ccagagaggaagggccgctgcactgcccggcctt   515
534  gagcctgggcattcccagagaggaagggccgctgcactgcccggcctt   583
```

Fig. 9B

```
516 cagaaagacagaattgcatcacccaatgcaggggagctttcctggacn 565
    ||||||||||||||||||||||||||||||||||||||||||||||| :
584 cagaaagacagaattcatcacccaatgcaggggagcattcctcgtcc  633

566 nagggaggngccgctcnttcaccaaacaaactgtgtctcatctgccagg 615
    : || ||  ||
634 aagggag.......................................  640

616 aaagaccagctcactcctgggaacngtcctggcaggctgggcccc    665
              ||||||||||||||| :||||||||||||||||
641 .........agcctcactcctgggaactgtcctggcaggtaggctgggcccc 683

666 cagtgctgttagaataaaagcctcgtgccgg  697 HSU618
    ||||||||||||||  ||||||||||| |||
684 cagtgctgttagattaaaaatccctcgtgctgg 715 TADG-5
```

Fig. 9C

```
  1 cggcncgagc tcgtgccgct tcggttcgct cccaggacccc cgggcagcgg
 51 ctggtgctgg accgggctgc ccggctgcgt cncatcaacc ggcagctgga
101 ggccctggag aatgactact ttcaggatga ctcccatcgg gactccctcn
151 nctcggcaag agactgcctc agtttgatta ctattcggac actgaaaga
201 aanagaanaa naatacccga ggtgatcatt ttaaacttcg cttccgaaaa
251 aactttcagg ccctgttgga ggagcagaac ttgagtgtgg ccgagggcct
301 aactacctga cggcctgtgc gggaccccca tcgcggcccc agcgccccctt
351 ctgtgctgtc tgtggcttcc catccccccta cacctgtgtc agctgcggtg
401 cccggtactg cactgtgcgc tgtctgggga cccaccagga gaccaggtgt
451 ctgaagtgga ctgtgtgagc ctgggcattc agacagaatt gggccgctgt
501 gcactgcccg gcctttcagaa agacagaatt gcatcaccca atgcaggggg
551 agcttttcct ggacnnaggg agggngccgct cnttcaccaa acaaaactgt
601 gtctcatctg ccaggaaaga ccagcttcac tcctgggaac ngtctggcag
651 gtaggctggg ccccccagtg ctgttagaat aaaaagcctc gtgccgg
```

Fig. 9D

| CLONE | SEQUENCE | PROMOTER | OVERLAP/IDENTITIES |
|---|---|---|---|
| 12 | 5'CTGGCAATCTGANTA3' | | |
| 14 | 5'CTGGCAATCTGACTA3' | EBV | 12bp/ 100% |
| 18 | 5'TAGTCGGATGGTATG3' | | |
| 13 | 3'GGAGTTGGGGAGAA5' | PKA-R1α(hs) | 12bp/ 90% |
| 16 | 5'TAACTGGGTTAGAT3' | | |
| 15 | 5'TTTGTGGGTGGGGG3' | HMG-14, ACTIN(hs) | 12bp/ 100% |
| 17 | 5'GGGTGGGGGGTGGC3' | INSULIN (hs) | 14bp/ 92% |
| 22 | 5'TGGGGGGAGCGAATA3' | | |
| 23 | 5'TGAATCATGGGGGAC3' | | |
| 19 | 3'CAGCGAATTGGAAAG5' | | |
| 20 | 5'ATTGGTTAAGGCGAC3' | | |

Fig. 11

| Clone No. | Sequences | Group |
|---|---|---|
| 12 | 5'tagtcagattgccag3' | I |
| 14 | 5'tagtcagattgccag3' | |
| 18 | 5'tagtcggatggtatg3' | |
| consensus | tagtc-gat-g---g | |
| 13 | 3'ggagttgggggagaa5' | II |
| 16 | 5'taactgggttagat3' | |
| 15 | 5'tttgtgggtgggggg3' | |
| 17 | 5'gggtgggggggtggc3' | |
| 22 | 5'tggggggagcgaata3' | |
| 23 | 5'tgaatcatgggggac3' | |
| consensus | tggggg | |
| 19 | 5'gaaaggttaagcgac3' | III |
| 20 | 5'attggttaaggcgac3' | |
| consensus | ggttaag | |

Fig. 12

SH3-CONTAINING PROTEIN, DNA AND USES THEREOF

CROSS-REFERENCE TO RELATED APPLICATION

This application is a continuation-in-part of U.S. Ser. No. 08/871,732 filed Jun. 9, 1997 now abandoned, and claims the benefit of priority under 35 USC §120.

BACKGROUND OF THE INVENTION

1. Field of the Invention

The present invention encompasses a protein designated TADG5 comprising an SH3 domain, a TADG5 DNA segment coding for the TADG5 protein, chimeric cells comprising the TADG5 DNA segment, vectors and plasmids comprising the TADG5 DNA segment and methods for producing the TADG5 protein as well as methods for using the TADG5 protein.

2. Description of the Related Art

Proteins containing SH3 domains have been previously identified. For example, chimeric protein tyrosine kinases comprising SH3 and SH2 domains are disclosed in U.S. Pat. No. 5,439,819. Proteins possessing SH2 and SH3 domains have been found to be important in cell cycle processes, especially in signal transduction pathways. Cyclin-dependent kinases possessing SH3 domains are well known participants in signal transduction processes. SH2 domains interact specifically with various proteins containing phosphotyrosine residues, whereas SH3 regions bind guanine nucleotide releasing factors, believed to be involved in important signaling pathways. The role in signal transduction of numerous molecules possessing SH3 and SH2 domains are discussed by Koch et al. (*Science* 252:668–674 (1991)).

Interfering in the intracellular signal transduction pathways provides mechanisms for numerous therapeutic applications. While several proteins have been identified that interfere with various signal transduction mechanisms, novel proteins involved in signal transduction pathways are important to provide alternatives for therapy and drug development. The novel protein of the invention provides a heretofore unknown molecule which binds to the promoter region of a number of important genes and the Epstein-Barr virus.

A partial DNA sequence called HSU618 has 95% homology over approximately 560 nucleotides to the TADG5 gene (GenBank Accession No. U61837; submitted by F. Xu from the University of Southern California). The HSU618 sequence does not contain an open reading frame, and instead, contains stop codons in all reading frames. The sequence does, however, exhibit high homology with the TADG5 gene starting at nucleotide 87 of the TADG5 sequence through approximately base 654. HSU618 is indicated to have the capacity to bind cyclin G proteins. Because the HSU618 fragment lacks an open reading frame, it cannot be expressed to produce the corresponding protein fragment, nor could it be said to suggest the TADG5 protein amino acid sequence nor to disclose the isolated and purified DNA segment coding for the TADG5 protein.

The prior art is deficient in lack of the nucleotide and amino acid sequence of the SH3 domain-containing TADG5 protein. The present invention fulfills this long-standing need and desire in the art.

SUMMARY OF THE INVENTION

The present invention encompasses a novel TADG5 protein having the amino acid sequence set out in SEQ ID No. 1, TADG5 DNA segments coding for the TADG5 protein, including a DNA segment isolated from human genetic material set out in SEQ ID No. 2, or a construct comprising the open reading frame found beginning at nucleotide 71 (with the methionine codon) to base 532, or optionally through nucleotide 535 (end of the in-frame stop codon downstream of the open reading frame). Preferably, the open reading frame segment from nucleotides 71 through 532 or 535 is coupled with a promoter segment and optionally coupled with additional DNA coding sequences useful in purification, such as a polyhistidine tail or an enzyme, such as GST.

In one embodiment of the present invention, there is provided an isolated TADG5 protein having the amino acid sequence of SEQ ID No. 1 or an allelic variant of SEQ ID No. 1 which retains the biological activity of the TADG5 protein. Further provided is an isolated DNA segment having the nucleotide sequence of SEQ ID No. 2 or an allelic variant thereof which encodes a protein having TADG5 biological activity. Additionally embodied are chimeric host cell comprising the above-described DNA segment, and antibodies directed towards a TADG5 protein, an allelic variant retaining TADG5 biological activity or functional fragments thereof.

In another embodiment of the present invention, there is provided an expression vector, comprising, in operable 5' to 3' linkage: (a) a promoter; and (b) a DNA segment encoding a TADG5 protein. Chimeric host cells comprising the expression vector are additional embodiments.

The above-referenced expression vector may further comprise: a signal sequence which is 3' of the promoter and 5' of the DNA segment encoding a TADG5 protein; a DNA sequence encoding a purification tag which is 5' or 3' of the DNA segment encoding a TADG5 protein; a linker sequence which is between the DNA sequence encoding a purification tag and the DNA segment encoding a TADG5 protein and encodes a cleavage site; transcriptional terminators and/or polyA sequences which are 3' of the DNA segment encoding a TADG5 protein; and/or a gene encoding a selectable marker.

In yet another embodiment, there is provided a method of protein production, comprising the steps of: (a) introducing the above-described expression vector into a host cell; and (b) providing any necessary factors required by the promoter for expression of the gene encoding the TADG5 protein.

In still yet another embodiment, there is provided a peptide derived from the TADG5 protein shown in SEQ ID No. 1 or a biologically active allelic variant thereof, wherein the peptide is further characterized by binding to an oligonucleotide having the sequence selected from the group consisting of SEQ ID Nos. 3, 4, 5, 6, 7, 8, 9, 10, 11, 12, 13 or a strand complementary to one of the preceding sequences. Included in this embodiment is a method of regulating gene expression, comprising the steps of: binding the peptide(s) to a gene to increase or decrease expression of the gene.

In yet another embodiment, there is provided a method of identifying TADG5-binding DNA regulatory regions, comprising the steps of: (a) treating a DNA sample with a cleavage agent to produce DNA segments; and (b) binding the DNA segments to a TADG5 protein, allelic variants, or functional fragments thereof to produce TADG5-bound DNA segments. Generally, the TADG5-bound DNA segments comprise TADG5-binding DNA regulatory regions. Subsequently, the the TADG5-bound DNA segments can be isolated, and if so desired, released from the TADG5 protein.

In yet another embodiment of the present invention, there is provided a method of regulating gene expression, comprising the step of: binding to a regulatory region of a gene a molecule selected from the group consisting of: (a) a TADG5 protein, allelic variants retaining TADG5 biological activity or functional fragments thereof; (b) single-stranded homologous oligonucleotides which are homologous to sequences that bind a TADG5 protein, allelic variants retaining TADG5 biological activity or functional fragments thereof; (c) single-stranded complimentary oligonucleotides which are complimentary to sequences that bind a TADG5 protein, allelic variants retaining TADG5 biological activity or functional fragments thereof; (d) an antibody directed towards a TADG5 protein, allelic variants retaining TADG5 biological activity or functional fragments thereof; and (e) an antisense RNA molecule directed towards a TADG5 transcript, allelic variants retaining TADG5 biological activity or functional fragments thereof.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 2 illustrates the sense nucleotide sequence of the TADG5 gene isolated from a cDNA ovarian library showing the open reading frame (ORF), initiation codon (Met), in-frame stop codon upstream of the ORF, in-frame stop codon downstream of the ORF, and the polyadenylation signal.

FIGS. 6A and 6B show amino acid alignments of the SH3 domain of TADG5 with known SH3 domains showing the conserved amino acids between these domains.

FIG. 6B is a comparison of SH3 domains of TADG5 and VAV.

FIG. 7 shows a comparison of TADG5's zinc finger domain to putative or known zinc finger domains of transcription factor 3 (TF3) and two yeast zinc finger domains showing the conserved nature of the appropriate cysteines and histidines.

FIGS. 9A–9D are a sequence comparison of TADG5 (SEQ ID No. 2) to the partial cDNA sequence of human putative cyclin G1 interacting protein (HSU618, SEQ ID No. 16) showing 95% homology over approximately 560 nucleotides of the TADG5 gene.

FIG. 9B shows the cDNA sequence of human HSU618 gene (SEQ ID No. 16).

FIG. 11 identifies clones isolated using the CASTing approach showing nucleotide sequence and percent identity to known promoter region sequences.

FIG. 12 lists subgroups of the isolated cloned nucleotide sequences.

DETAILED DESCRIPTION OF THE INVENTION

Figure 1A:
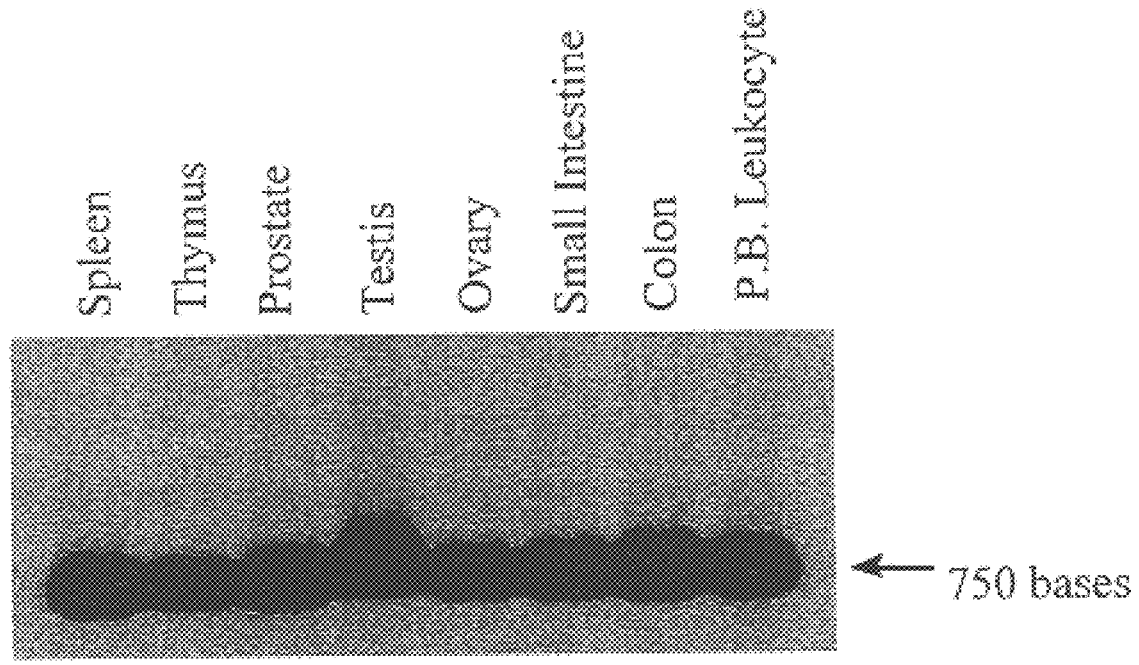
FIGS. 1A and 1B show a Northern blot analysis demonstrating that the TADG5 gene is transcribed in adult and fetal tissues.

The present invention is directed towards an isolated TADG5 protein having the amino acid sequence of SEQ ID No. 1 or an allelic variant of SEQ ID No. 1 that retains the biological activity of a TADG5 protein, as well as an isolated DNA segment encoding the TADG5 protein or allelic variant thereof. Additionally, vectors comprising this DNA segment and chimeric host cells comprising those vectors are provided by the present invention. The present invention further provides an antibody directed towards a TADG5 protein, an allelic variant retaining TADG5 biological activity or functional fragments thereof.

The present invention is directed towards an isolated DNA segment having the nucleotide sequence of SEQ ID No. 2 or an allelic variant of SEQ ID No. 2 which encodes a protein having TADG5 biological activity, vectors comprising these DNA segments, and chimeric host cells comprising those vectors.

The present invention is further directed towards an expression vector, comprising, in operable 5' to 3' linkage: (a) a promoter; and (b) a DNA segment encoding a TADG5 protein. The invention is additionally directed towards chimeric cells comprising this expression vector.

The above-referenced expression vector may further comprise any or all of the following components: a signal sequence which is 3' of the promoter and 5' of the DNA segment encoding a TADG5 protein; a DNA sequence encoding a purification tag which is 5' or 3' of the DNA segment encoding a TADG5 protein; a linker sequence which is positioned between the DNA sequence encoding a purification tag and the DNA segment encoding a TADG5 protein and encodes a cleavage site; transcriptional terminators and/or polyA sequences which are 3' of the DNA segment encoding a TADG5 protein; and a gene encoding a selectable marker.

The present invention is further directed towards a method of protein production, comprising the steps of: (a) introducing the above-described expression vector into a host cell; and (b) providing any necessary factors required by the promoter for expression of the gene encoding the TADG5 protein. Preferably, the DNA segment encoding a TADG5 protein is SEQ ID No. 2 or an allelic variant encoding a biologically active TADG5 protein.

The present invention is further directed towards a peptide derived from a TADG5 protein or biologically active allelic variant thereof. The peptide is further characterized by binding to an oligonucleotide having the sequence shown in SEQ ID Nos. 3, 4, 5, 6, 7, 8, 9, 10, 11, 12, 13 or a strand complementary to one of the preceding sequences. Additionally, the present invention further provides for a method of regulating gene expression, comprising the steps of: binding the above-described peptide(s) to a gene to increase or decrease expression of the gene.

The present invention still further provides for a method of identifying TADG5-binding DNA regulatory regions, comprising the steps of: (a) treating a DNA sample with a cleavage agent to produce DNA segments; and (b) binding the DNA segments to a TADG5 protein, allelic variants, or functional fragments thereof to produce TADG5-bound DNA segments. Generally, the TADG5-bound DNA segments comprise TADG5-binding DNA regulatory regions. This method may further comprise isolating the TADG5-bound DNA segments and may still further comprise releasing the DNA segment bound to the TADG5 protein, biologically active allelic variant or functional fragments thereof.

The present invention is further directed towards a method of regulating gene expression, comprising the step of: binding to a regulatory. region of a gene a molecule selected from the group consisting of: (a) a TADG5 protein, allelic variants retaining TADG5 biological activity or functional fragments thereof; (b) single-stranded homologous oligonucleotides which are homologous to sequences that bind a TADG5 protein, allelic variants retaining TADG5 biological activity or functional fragments thereof; (c) single-stranded complimentary oligonucleotides which are complimentary to sequences that bind a TADG5 protein, allelic variants retaining TADG5 biological activity or functional fragments thereof; (d) an antibody directed towards a TADG5 protein, allelic variants retaining TADG5 biological activity or functional fragments thereof; and (e) an antisense RNA molecule directed towards a TADG5 transcript, allelic variants retaining TADG5 biological activity or functional fragments thereof. Preferably, the homologous oligonucleotides are SEQ ID Nos. 3, 4, 5, 6, 7, 8, 9, 10, 11, 12 or 13, and the complementary oligonucleotides are complementary to SEQ ID Nos. 3, 4, 5, 6, 7, 8, 9, 10, 11, 12 and 13.

The TADG5 protein comprises an SH3 domain, a zinc finger, a basic amino acid rich region, as well as a potential phosphorylation site. Nucleotide sequences which bind to the TADG5's zinc finger motif have been identified in several important genes including protein kinase A regulatory subunit gene ($R_{1\alpha}$), Epstein-Barr virus, gastrin, GADPH, beta-actin, HMG-14, Complement C5, and insulin. Of course, the protein is useful as a source of amino acids, as a nutrition supplement, and as a marker for human tissue, as well as its primary role in cell cycle control. In addition, the protein itself or peptides generated from the protein sequence are useful as antigens for the production of polyclonal and monoclonal antibodies. Further, the gene itself is used as an antisense vehicle for cell cycle control by shutting down signaling or cell division. The cyclin proteins are known binders of cyclin-dependant kinase. As this process is part of the activation for the cell cycle control system and the cyclin complex also binds with tumor suppressor genes, cyclins have been found to be potent inhibitors of the cell cycle progression. The TADG5 gene is a binding partner for the cyclin-G proteins as demonstrated by the fact that the fragmentary sequence HSU618 was found to be associated with cyclin-G proteins, and has a high degree of homology with the TADG5 gene.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (2nd Ed.)", (1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. DNA structures are discussed herein according to the normal convention of giving only the sequence in the 5' to 3' direction along the nontranscribed strand of DNA (i.e., the strand having a sequence homologous to the mRNA). The term "peptide" or "polypeptide" is defined as several (i.e., multiple) amino acids attached together.

A "vector" is a replicon, such as plasmid, phage or cosmid, to which another DNA segment may be attached so as to bring about the replication of the attached segment. Specifically as used herein, the term "vector(s)" means plasmid, cosmid, phage or any other vehicle to allow insertion, propagation and expression of TADG5 cDNA. A "replicon" is any genetic element (e.g., plasmid, chromosome, virus) that functions as an autonomous unit of DNA replication in vivo; i.e., capable of replication under its own control. An "origin of replication" refers to those DNA sequences that participate in or direct DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with a particular host. The expression vector typically contains an origin of replication, promoter(s), terminator(s), as well as specific genes which are capable of providing phenotypic selection in transformed cells (i.e., selectable markers). The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. Specifically as used herein, "DNA coding for a protein" means DNA sequences which produce a particular primary amino acid sequence. The boundaries of the coding sequence are determined by a start codon at the 5' (amino) terminus and a translation stop codon at the 3' (carboxyl) terminus. A coding sequence can include, but is not limited to, prokaryotic sequences, a cDNA from eukaryotic mRNA, genomic DNA sequences from eukaryotic (e.g., mammalian) organisms and even synthetic DNA sequences. A polyadenylation signal and transcription termination sequence will usually be located 3' of the coding sequence. A "cDNA" is defined as copy DNA or complementary DNA and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with proteins that upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. Specifically as used herein, the term "promoter(s)" means regulatory DNA sequences that control transcription of the TADG5 cDNA. For purposes of defining the present invention, a minimal promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain the −10 and −35 consensus sequences, and additionally, ribosomal binding Shine-Dalgarno sequences. As used herein, "promoter" may also refer to an intact regulatory sequence directing transcription (and subsequent translation) of a coding sequence, and may include any or all of the above-mentioned transcriptional and translational control sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The exact length of the primer will depend upon many factors, including temperature, source of primer and use the method. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and a polymerizing agent, such as a DNA polymerase, and at a suitable temperature and pH. The primer may be either single-stranded or double-stranded and must be sufficiently long to prime the synthesis of the desired extension product in the presence of the polymerizing agent. For example, for diagnostic applications, depending on the complexity of the target sequence, the oligonucleotide primer typically contains 15–25 or more nucleotides, although it may contain fewer nucleotides.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced into the cell. Specifically as used herein, the term "transformation" or "transfection" means incorporation permitting expression of heterologous DNA sequences by a cell. The transforming DNA may or may not be integrated (covalently linked) into the genome of the cell. In prokaryotes, yeast, and mammalian cells, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes, but also eukaryotes such as yeast, plant and animal cells. Specifically as used herein, the term "host(s)" means any cell that will allow or direct TADG5 expression. Specifically as used herein, "chimeric cell" means a cell whose DNA has been altered compared to a normal cell of the same organism. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and plant cells, such as *Arabidopsis thaliana* and *Tobaccum nicotiana*.

As used herein, "fragment," as applied to a polypeptide, will ordinarily be at least 10 amino acid residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis. The ability of a candidate fragment to to bind to a particular DNA sequence can be assessed by methods described herein. Purified fragments or antigenic fragments can be used to isolate regulatory regions or to generate new regulatory enzymes (e.g., using multiple functional fragments from different enzymes), as well as to generate antibodies, all employing standard protocols known to those skilled in the art. As used herein, "functional fragment" is meant to encompass not only those peptide fragments retaining biological activity, but also those peptide fragments that retain binding specificity to a particular nucleotide sequence.

As described herein, a standard Northern blot assay can be used to ascertain the relative amounts of mRNA in a cell or tissue in accordance with conventional Northern hybridization techniques known to those persons of ordinary skill in the art. Alternatively, a standard Southern blot assay may be used to confirm the presence, the copy number and/or the position of a gene in accordance with conventional Southern hybridization techniques known to those of ordinary skill in the art. Both the Northern blot and Southern blot use a hybridization probe, (e.g., radiolabelled full-length or partial cDNA) of at least 20 (preferably at least 30, more preferably at least 50, and most preferably at least 100) consecutive nucleotides in length. The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA Blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The term "allelic variant", "substitution analog" or "allelic variation" all refer to a DNA sequence in which one or more codons specifying one or more amino acids of TADG5 or a TADG5 polypeptide are replaced by alternate codons that specify the same amino acid sequence with a different DNA sequence. Where "allelic variant" or "substitution analog" refers to a protein or polypeptide, it means the substitution of a small number, generally five or less, of amino acids wherein the biological activity of the protein is maintained.

The following examples are given for the purpose of illustrating various embodiments of the invention and are not meant to limit the present invention in any fashion:

EXAMPLE 1
Gene Isolation and Expression

Figure 1B:
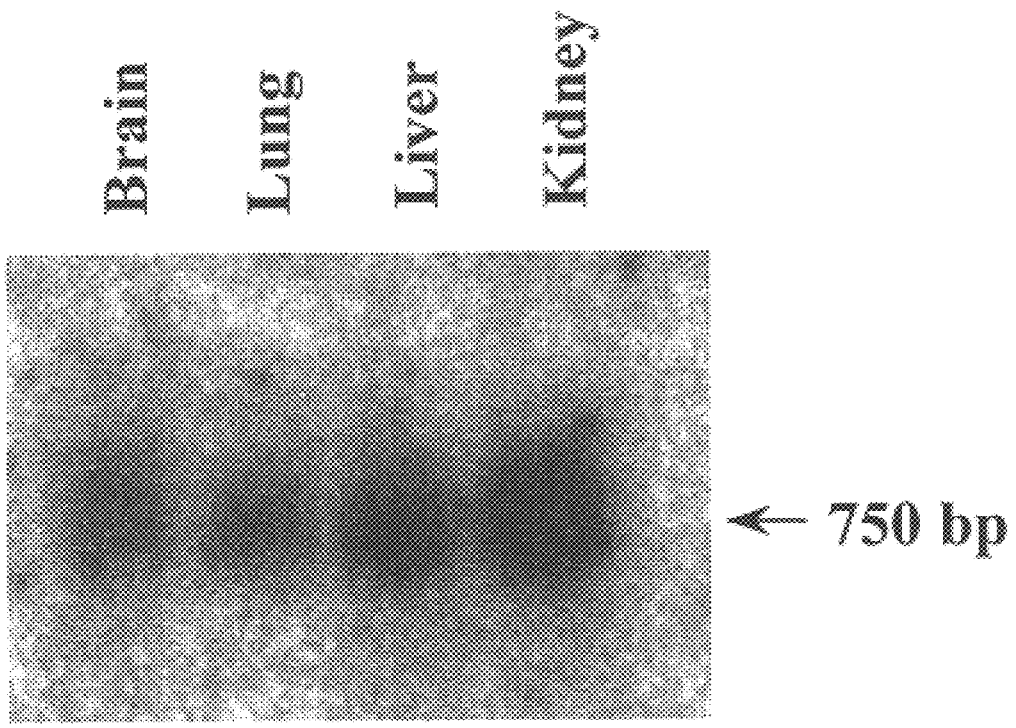

A novel gene, named TADG5, was identified and isolated as a PCR product differentially displayed between normal and ovarian carcinoma mRNA, and amplified using redundant primers for an SH3 domain. The PCR band selected, based on differential expression in tumor cDNA, was subcloned as a 300 base pair amplified PCR product and sequenced. Specific primers synthesized to the 300 base pair sequence allowed gene amplification. The PCR product was used as a probe in Northern blot analysis to show that the novel TADG5 gene is expressed in adult and fetal tissues as an approximately 750 nucleotide mRNA (FIGS. 1A and 1B). The TADG5 gene was shown to be expressed in adult tissues including; spleen, thymus, prostate, testes, ovary, small intestine, colon and leukocytes, as well as fetal tissues including; brain, lung, liver and kidney.

The PCR product produced by the above method was used subsequently as a probe to screen an ovarian cDNA library resulting in isolation of a positive clone containing 735 base pairs, including a poly-A tail (FIG. 2). The isolated sense DNA sequence of this clone includes an open reading frame with a nucleotide stop codon upstream from the open reading frame, and a stop codon followed by a polyadenylation signal downstream from the open reading frame. 5'-RACE PCR, for example, using 5' anchored human lung cDNA further confirmed the 5' end of the novel gene and confirmed the sequence of the first 22 base pairs of the ovarian clone.

Figure 3:
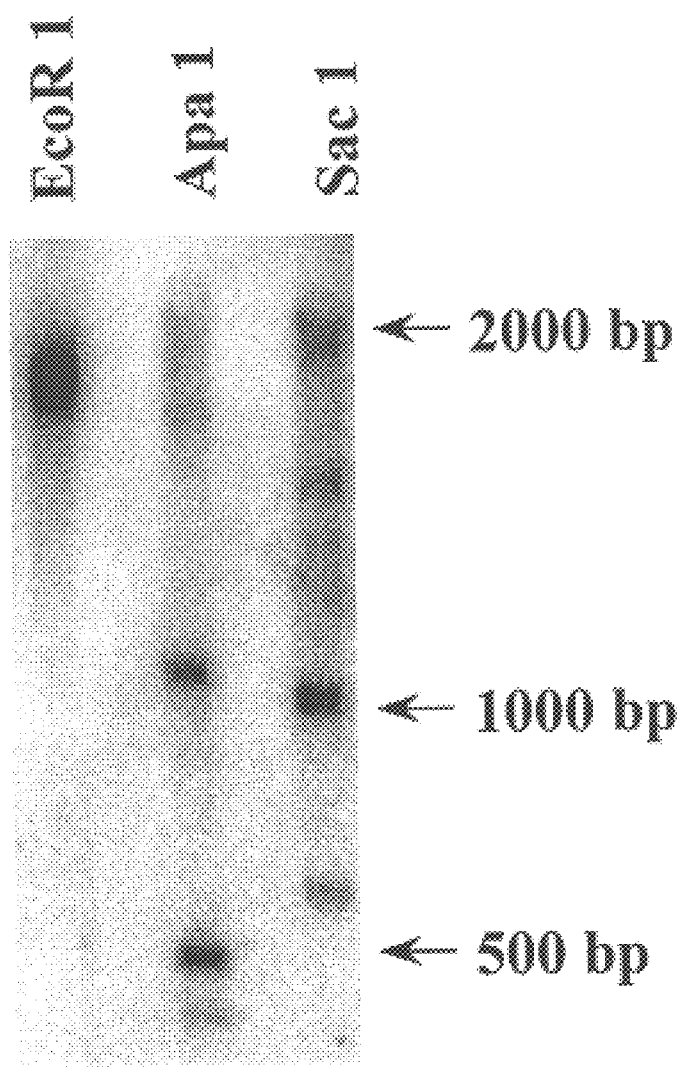
FIG. 3 shows a Southern blot analysis of ovarian genomic DNA showing the presence of the TADG5 gene in the human genome.
Figure 4:
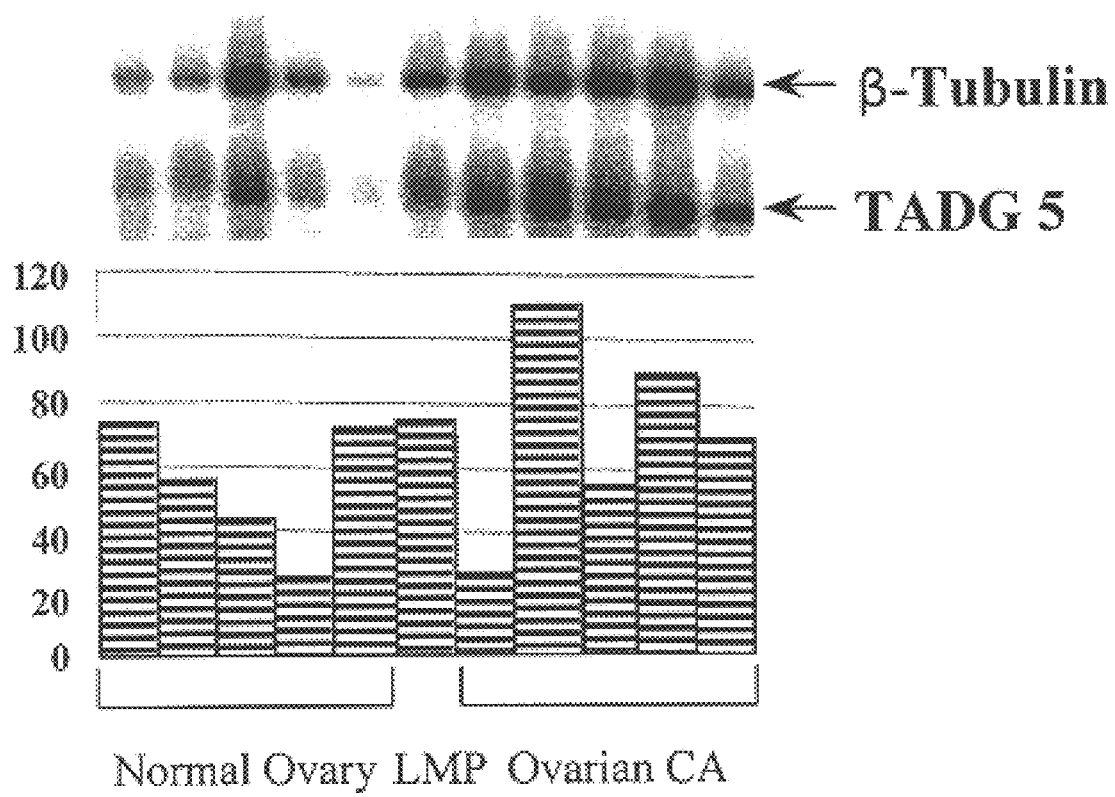
FIG. 4 is a quantitative PCR of the TADG5 gene showing that the TADG5 gene is expressed both in normal and tumor cDNA and that the TADG5 gene is over-expressed in ovarian tumors relative to normal ovary.

The TADG5 gene was identified in ovarian genomic DNA. The ovarian cDNA clone was used as a probe for Southern blot analysis to confirm the presence of the TADG5 gene in ovarian genomic DNA (FIG. 3). The TADG5 gene contains known restriction sites for ApaI and SacI restriction enzymes as determined from the ovarian cDNA clone sequence and as demonstrated by the presence of two or more bands as expected for these restriction enzyme digested lanes. Primers specific to internal sequences of the TADG5 gene were constructed. The cDNA from both normal, low malignant potential tumors and ovarian carcinomas can be quantitatively amplified in the presence of an internal control gene (such as β-tubulin) to show that the TADG5 gene is expressed both in normal and tumor cDNA as shown in FIG. 4. These data demonstrate that TADG5 is over-expressed in high malignant potential tumors.

EXAMPLE 2
The TADG5 Protein

Figure 5:
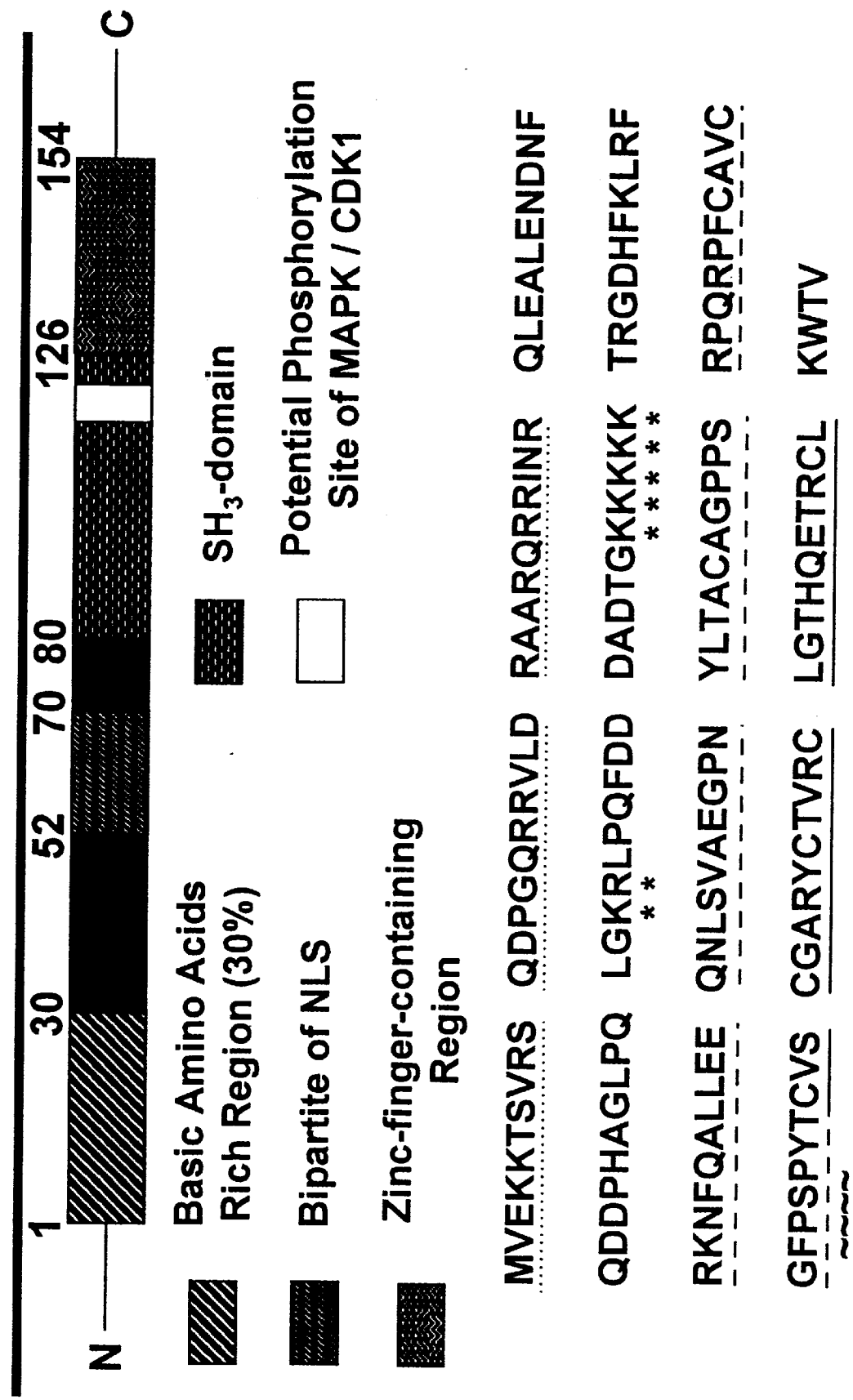
FIG. 5 is a diagram of the TADG5 protein showing the amino acid sequence and the various functional domains, including an SH3 domain, a zinc finger, a basic amino acid rich region, a bipartite nuclear localization sequence as well as a potential phosphorylation site.

The invention provides a novel isolated and purified TADG5 DNA sequence coding for the TADG5 protein. The open reading frame of the TADG5 nucleotide sequence predicts a 154 amino acid protein with the initial codon for methionine at position 71 of the sequence. This continues through position 532 where a stop codon is identified. Examination of the 154 amino acid sequence demonstrates several conserved functional domains as illustrated in FIG. 5. Beginning at the amino terminal end, the first 30 amino acids are recognized as a basic amino rich region. Downstream from this region at amino acid 52–70, a bipartite nuclear localizing sequence is recognized. Further downstream at amino acid 80, a putative SH3 domain is recognized and extends approximately 50 amino acids downstream. Downstream from the SH3 domain, a potential phosphorylation site for the map kinase enzyme is recognized. Finally, at the carboxyl terminal contains putative zinc fingers.

These functional domains of the TADG5 protein indicate that this novel protein is a component of the signal transduction pathway system and that it interacts with other proteins through its SH3 domain. An alignment of amino acids in the SH3 domain confirms conserved amino acids in accordance with the general configuration of SH3 domains of known proteins (FIGS. 6A and 6B). The bipartite nuclear localizing domain indicates that the TADG5 protein is localized in the nucleus and that the protein interacts with DNA, either through the basic amino acid domain or through the zinc finger motif, or through both domains working in concert. A comparison of the zinc finger motif with known zinc fingers in both the TF3 (transcription factor 3) protein and in two yeast zinc finger proteins demonstrates the conserved nature of the appropriate cysteines and histidines to create such a zinc finger (FIG. 7). Lastly, the TADG5 protein has the capacity to be activated and inactivated through phosphorylation by the map kinase signal system.

EXAMPLE 3

Production of TADG5 Protein and Expression Vectors

The invention provides a method of producing the TADG5 protein. For example, after synthesizing specific primers to allow amplification of the complete open reading frame sequences the TADG5 DNA sequence can be integrated into a vector, and the TADG5 protein expressed in a chimeric cell using standard techniques as set out in "Molecular Cloning, A Laboratory Manual", 2nd Edition, Cold Spring Harbor Laboratory Press (1989). Optionally, the protein may be expressed as a fusion product such as with the carboxyl terminal region of the glutathione S-transferase ("GST") protein using a chimeric cell, such as an E. coli bacterial expression system.

The cDNA coding for the TADG5 protein is preferably inserted into an expression vector and expressed in a suitable host cell. The promoter useful in the present invention may be any that allows regulation of the transcription of the TADG5 cDNA. Preferably, the promoter is $P_{tac}$ or $P_{lac}$ incorporated in the pGEX series of expression vectors available from Pharmacia (Uppsala, Sweden; www.biotech.pharmacia.se). Alternatively, one of the many different promoters known to those skilled in this art may be used. A signal sequence useful in the present method may be any that contains a translation initiation codon and secretory signal together with part of a coding region for a highly expressed gene endogenous to the host cell. Preferably signal sequences are those of the pGEX vector series.

The linker sequence useful in the present method contains a recognition sequence for any proteolytic enzyme, preferably a thrombin recognition sequence, as in the pGEX vector series.

The transcription terminators and/or polyA sequences useful in the present method may be any that allows stabilization and correct termination of the TADG5 mRNA transcripts. Many different transcription terminator and/or polyA sequences are known to those skilled in this art but the inventors prefer using those available from the pGEX vector series.

The selectable marker gene useful in the method of the present invention may be any that permits isolation of cells transformed with a TADG5 cDNA plasmid. Preferably, the selectable marker gene is selected from pyr4, pyrG, argB, trpC, amdS, phleomycin or other antibiotic resistance genes.

Additionally, recombinant production of TADG5 protein is described below in its preferred embodiments. TADG5 can be produced in a number of host cells, such as Aspergillus; *Saccharomyces cerevisiae, Kluyveromyces lactis*, or *Pichia pastorsis*; insect cells such as SF9; and mammalian cells such as Cos cells, HeLa cells or the breast cancer tissue cell lines 231 and 435S, as well as prokaryotic cells such as E. coli. The host cells, preferably E. coli or mammalian cell lines, useful in the present invention are any that allow for integration of a vector, preferably a plasmid comprising the TADG5 cDNA and expression of the TADG5 cDNA.

The isolated DNA of SEQ ID No. 1 was inserted into an expression vector, pGEX, comprising a promoter, an initiation sequence, a DNA segment coding for GST, and a linker. The vector was transformed into E. coli and expressed.

Figure 8A:
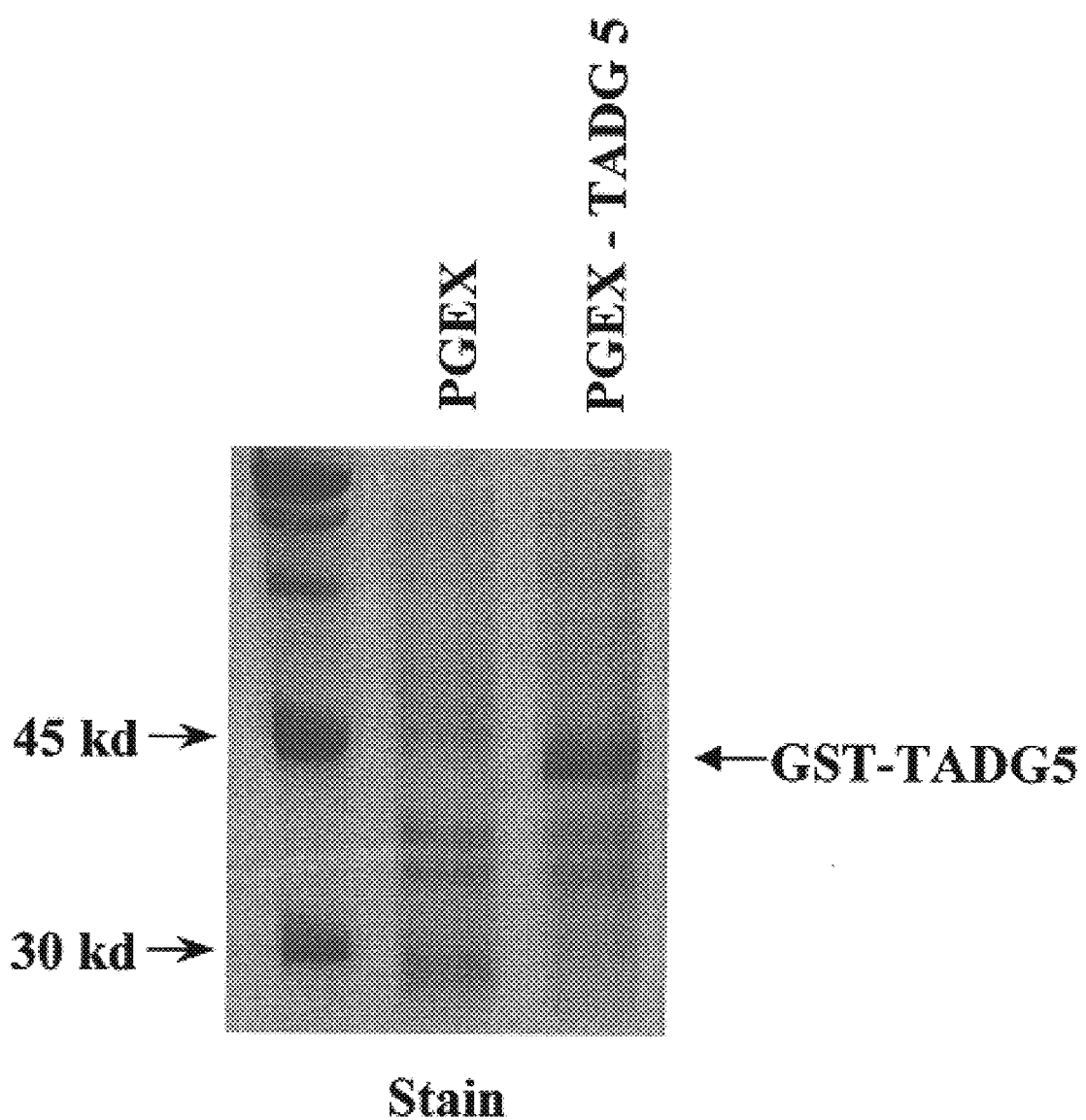
FIG. 8A shows polyacrylamide gel electrophoresis analysis of GST-TADG5 fusion proteins expressed in *E. coli* and stained with coomassie blue showing the molecular weight of the GST-TADG5 fusion protein to be 45 kd.

Molecular weight determination was performed by using polyacrylamide gel electrophoresis which confirmed expression of an anticipated 30 kD protein for the GST gene alone and a predicted 45 kD fusion product for the GST-TADG5 (FIG. 8A).

Figure 8B:
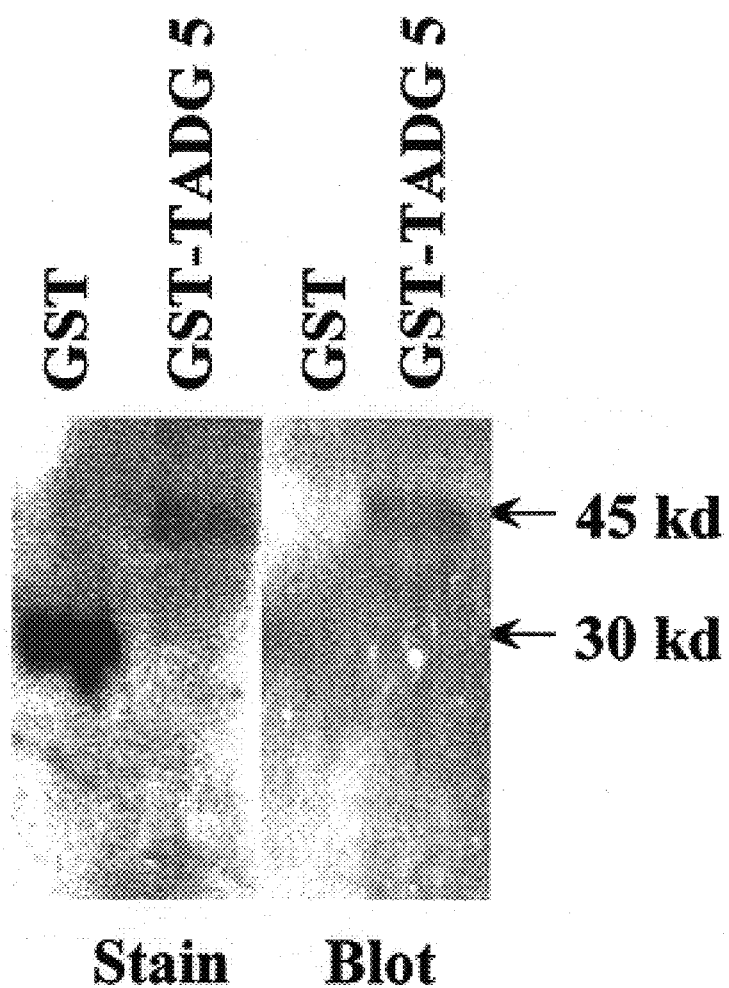
FIG. 8B shows a Western analysis of GST-TADG5 fusion proteins expressed in *E. coli* confirming the expression of TADG5 in this bacterial expression system.

The invention further provides generation of antibodies against peptides of the novel protein. For example, peptides synthesized from the amino and carboxy terminal ends of the TADG5 amino acid sequence were used to raise polyclonal antibodies, which in turn were used to confirm expression of TADG5 as a GST fusion protein in E. coli. Western analysis confirmed expression of this protein in this particular expression system (FIG. 8B). Other polyclonal antibodies developed against peptides to the various functional domains also allow for the identification of interacting proteins and nucleotide sequences with the TADG5 protein. Interruption of such interactions through the SH3 domain, map kinase phosphorylation motif, basic amino acid domain and/or zinc finger motif may be useful in restoring control of the cell cycle in certain tumor types.

As noted, a partial sequence recently entered into the database called HSU618 has about 95% homology over approximately 560 nucleotides to the TADG5 gene. The HSU618 sequence (SEQ ID No. 16) does not contain an open reading frame and contains many stop codons in all reading frames. Therefore, the sequence of HSU618 neither discloses the novel protein nor can the sequence be cloned and expressed to yield the novel protein. The HSU618 sequence does, however, have a high homology with the TADG5 gene starting at nucleotide 87 of the TADG5 sequence and covering the TADG5 sequence through approximately base 654, as shown in FIGS. 9A–9D. This suggests that TADG5 may have the capacity to bind cyclin G proteins as the HSU618 sequence was identified based on its capacity to associate with cyclin G proteins. The cyclins are known binders of cyclin-dependent kinase. Cyclin binding with cyclin-dependent kinase is part of the activation for the cell cycle control system. The cyclin/cyclin dependent kinase complex also binds with tumor suppressor genes, and as such, are inhibitors of the cell cycle progression. TADG5 may act as a binding partner for the cyclin-G proteins. A comparison of the sequence differences between HSU618 and TADG5 gene is shown in FIGS. 9A and 9B.

The invention further provides a method of using the novel protein produced and isolated by the above method. The isolated fusion protein is hydrolyzed, for example, with pepsin, trypsin, chymotrypsin, elastase, carboxypeptidase, aminopeptidase and/or dipeptidase to produce smaller peptide fragments and individual amino acids, in order to provide essential and nonessential amino acids of nutritional importance (Harper AE, Amino acids of nutritional importance, In Toxicants occurring naturally in foods, ed. Committee on Food Protection, Food and Nutritional Board, National Research Council, 2nd ed. Washington, D.C.: National Research Council, 1973).

EXAMPLE 4

Identification of Binding Sequences

The invention further provides an additional method for using the TADG5 protein. Expression of the GST-TADG5 fusion product in a bacterial expression system, for example, allows direct evaluation of the DNA-binding capacity of the TADG5 protein, either through the basic amino acid region domain or the zinc finger motif. E. coli was used to express the fusion product, and the expressed, secreted fusion protein was subsequently isolated from other proteins by binding of the GST moiety to glutathione-conjugated sepharose beads as follows. Host cells were ruptured by sonication, and the fusion protein was bound to Glutathione Sepharose 4B equilibrated with 2 ml of 50% slurry to each 100 ml of sonicate in 1× PBS including 1% Triton X-100 and 1 mM PMSF. The resulting mixture was incubated 15 mins with gentle agitation, then at 4° C. overnight. The suspension was then centrifuged at 500×g for 5 min to sediment the matrix. The supernate was removed and the pellet washed with 10 bed volumes of 1× PBS (bed volume is 0.5×volume of 50% Glutathione Sepharose slurry used). The suspension was centrifuged at 500×g for 5 min to sediment the matrix and the wash discarded. This wash was repeated three times. The fusion protein was eluted by addition of a buffer (10 mM glutathione and 50 mM Tris-HCL (pH 8.0)) equal in volume to the bed volume of the washed, sedimented matrix. The sediment/buffer was mixed gently to resuspend the matrix. The resulting suspension was incubated at room temperature (22–25° C.) for 10 min to elute the fusion protein from the matrix.

A "casting" technique (Hyde-DeRuyscher et al., 1995) was used to determine DNA binding sites for the TADG5 protein. Briefly, a 55 basepair oligonucleotide is synthesized that contains three parts. Part A and part C are the 5' and 3' ends of the oligonucleotide, respectively, and are primer binding sequences. Between parts A and C is part B, an approximately 15 base region containing all the different permutations of a random sequence. The TADG5 protein, used herein in the form of the GST-TADG5 fusion protein, is used to bind to the part B random sequences. Upon binding by TADG5, primers homologous to the primer binding sites part A and C are annealed to allow amplification of the part B internal sequence bound by TADG5. After multiple rounds of binding and amplification, the sequences recognized and bound by TADG5 are subcloned and sequenced.

Figure 10:
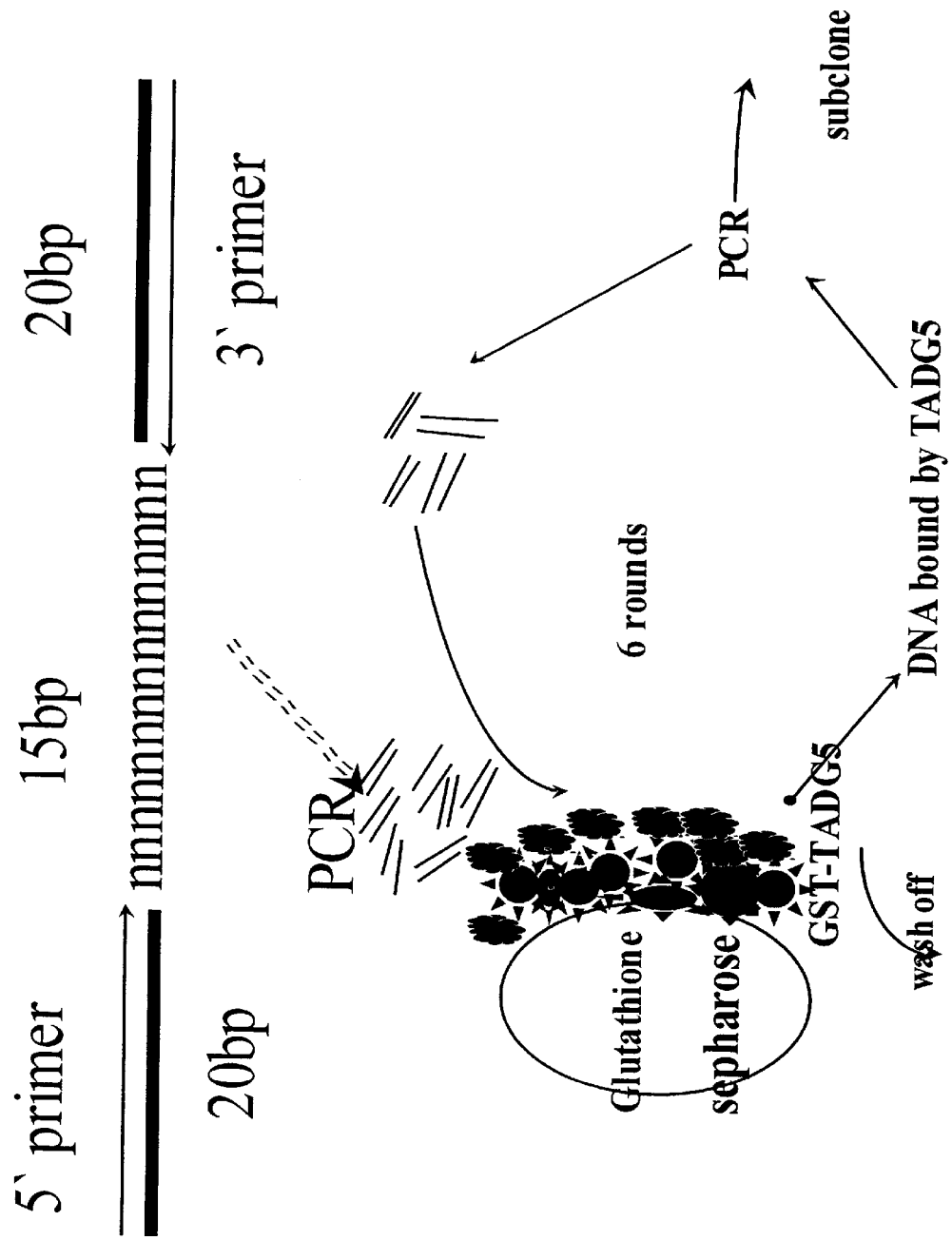
FIG. 10 illustrates the CASTing approach used to isolate nucleotide sequences that may bind to TADG5's basic amino acid rich region or zinc finger motif.

As shown in FIG. 10, nucleotide sequences that bind to either the basic amino acid region and/or the zinc finger motif of the TADG5 protein were isolated using the GST-TADG5 fusion protein. The sepharose:protein:DNA complexes were collected by centrifugation and washed. The DNA was purified from the complex, and subsequently cloned and sequenced. Eleven sequenced clones are shown in FIG. 11. They all have a core consensus sequence (underlined) and may be further subgrouped into three categories as indicated in FIG. 12. The clones were found to be DNA segments from the promoter regions of several genes as well as from the Epstein Barr Virus. The clones are useful as probes for identifying and amplifying the corresponding promoter regions or as binding agents to interfere with expression of the corresponding genes.

EXAMPLE 5

Preparation of Allelic Variants

Due to the redundancy of the DNA code, there are millions of DNA sequences that would produce the same amino acid sequence when expressed. Given the amino acid sequence of, for example, SEQ ID No. 1, one can substitute into the natural DNA sequence, such as SEQ ID No. 2, alternative codons for the desired amino acids to produce an alternative DNA sequence also coding for the novel protein. One may find that particular chimeric cells of a particular expression method favor particular mRNA codons for a particular amino acid. Altering the human DNA sequence to increase the frequency of favored codons may improve the expression efficacy in a chimeric cell, thus improving the efficacy of the expression process. The sequences may be derived by substitution of redundant codons for the amino acid sequences and splicing the substituted sequences into the natural gene by routine methods well known in the art. It is impractical to attempt to list all the millions of DNA sequences that may code for the claimed sequence. However, the invention comprises the novel protein, its novel amino acid sequence, and all DNA sequences natural or synthetic coding for the novel amino acid sequence.

These substitution analogs may be constructed in the following manner: Table 1 lists the alternative codons that code for the 20 common amino acids. DNA sequence substitution analogs that also code for human TADG5 can be constructed by choosing alternate codons from Table 1 to alter the DNA sequence between a pair of restriction enzyme cleavage sites, as are well known in the art. Alternative codons are assembled into a synthetic oligonucleotide by conventional methods and the synthetic oligo is substituted into the endonuclease treated DNA by the methods described in "Molecular Cloning. A Laboratory Manual", 2d Edition, Cold Spring Harbor Laboratory Press (1989), to produce a substitution analog. Other methods generally known to those skilled in the art can also be employed to obtain substitution analogs of DNA sequences.

The alteration of the DNA by cleavage and codon substitution may be repeated to substitute substantial portions of the original DNA sequence with alternative codons without altering the protein amino acid sequence. Alteration of a DNA sequence which produces no change in the protein expressed by the DNA sequence might, for example, be conducted to increase protein expression in a particular host cell by increasing the occurrence of codons that correspond to amino acid tRNAs found in higher concentration in the host cell. Such altered DNA sequences for substitution analogs can be easily produced by those of ordinary skill in the art following the method set out above, or other alternative techniques for altering the DNA sequence while obtaining the same protein on expression. Substitution analogs can be obtained by substitution of oligonucleotides at restriction cleavage sites as described above, or by other equivalent methods that change the codons while preserving the amino acid sequence of the expressed protein.

TABLE 1

| SYMBOL | | | |
|---|---|---|---|
| 1-Letter | 3-Letter | AMINO ACID | CODON USAGE |
| A | Ala | Alanine | GCT, GCC, GCA, GCG |
| C | Cys | Cysteine | TGT, TGC |
| D | Asp | Aspartic acid | GAT, GAC |
| E | Glu | Glutamic acid | GAA, GAG |
| F | Phe | Phenylalanine | TTT, TTC |
| G | Gly | Glycine | GGT, GGC, GGA, GGG |
| H | His | Histidine | CAT, CAC |
| I | Ile | Isoleucine | ATT, ATC, ATA |
| K | Lys | Lysine | AAA, AAG |
| L | Leu | Leucine | TTA, TTG, CTT, CTC, CTA, CTG |
| M | Met | Methionine | ATG |
| N | Asn | Asparagine | AAT, AAC |
| P | Pro | Proline | CCT, CCC, CCA, CCG |
| Q | Gln | Glutamine | CAA, CAG |
| R | Arg | Arginine | CGT, CGC, CGA, CGG, AGA, AGG |
| S | Ser | Serine | TCT, TCC, TCA, TCG, AGT, AGC |
| T | Thr | Threonine | ACT, ACC, ACA, ACG |
| V | Val | Valine | GTT, GTC, GTG, GTG |
| W | Trp | Tryptophan | TTG |
| Y | Tyr | Tyrosine | TAT, TAC |

Those skilled in the art will recognize that many variations are possible in substituting conserved amino acids in the protein sequence which will produce variations in sequence without seriously changing the biological activity of the protein. In addition, certain peptides may be made by selective enzymatic cleavage of the TADG5 protein or by synthesis of selected peptide sequences. These peptides will retain the binding characteristics of the intact protein and may be substituted for the protein in certain applications. Peptides may also be used to raise antibodies against the intact protein. SEQ ID Nos. 14 and 15 illustrate two peptides that were used to produce polyclonal antibodies which bind the TADG5 protein.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated TADG5 protein having the amino acid sequence of SEQ ID No. 1.

2. A peptide derived from the protein of claim 1, wherein said peptide is further characterized by binding to a single stranded oligonucleotide having the sequence selected from the group consisting of SEQ ID Nos. 3, 4, 5, 6, 7, 8, 9, 10, 11, 12, and 13 or by binding to a strand complementary to one of the preceding sequences.

3. A method of regulating expression of a TADG5 target gene in a cell, comprising the steps of:

contacting said cell with the peptide(s) of claim 2;

binding said peptide(s) to a regulatory region of said target gene, thereby regulating the expression of said gene.

4. A method of regulating expression of a TADG5 target gene, comprising the step of:

contacting a cell containing said TADG5 target gene with a molecule thereby regulating the expression of said gene, wherein said molecule is selected from the group consisting of:

a TADG5 protein or functional fragments thereof;

single-stranded homologous oligonucleotides, wherein said homologous oligonucleotides are homologous to sequences that bind a TADG5 protein or functional fragments thereof;

single-stranded complimentary oligonucleotides, wherein said complimentary oligonucleotides are complimentary to sequences that bind a TADG5 protein or functional fragments thereof;

an antibody directed towards a TADG5 protein or functional fragments thereof; and an antisense RNA molecule directed towards a TADG5 transcript or functional fragments thereof.

5. The method of claim 4, wherein said homologous oligonucleotides are selected from the group consisting of SEQ ID Nos. 3, 4, 5, 6, 7, 8, 9, 10, 11, 12 and 13.

6. The method of claim 4, wherein said complementary oligonucleotides are complementary to oligonucleotides selected from the group consisting of SEQ ID Nos. 3, 4, 5, 6, 7, 8, 9, 10, 11, 12 and 13.

* * * * *

SEQUENCE LISTING

<160> NUMBER OF SEQ ID NOS: 32

<210> SEQ ID NO 1
<211> LENGTH: 154
<212> TYPE: PRT
<213> ORGANISM: Homo sapiens
<220> FEATURE:
<223> OTHER INFORMATION: amino acid sequence of TADG5 protein

<400> SEQUENCE: 1

Met Val Glu Lys Lys Thr Ser Val Arg Ser Gln Asp Pro Gly Gln
                 5                  10                  15

Arg Arg Val Leu Asp Arg Ala Ala Arg Gln Arg Arg Ile Asn Arg
                20                  25                  30

Gln Leu Glu Ala Leu Glu Asn Asp Asn Phe Gln Asp Asp Pro His
                35                  40                  45

Ala Gly Leu Pro Gln Leu Gly Lys Arg Leu Pro Gln Phe Asp Asp
                50                  55                  60

Asp Ala Asp Thr Gly Lys Lys Lys Lys Thr Arg Gly Asp His
                65                  70                  75

Phe Lys Leu Arg Phe Arg Lys Asn Phe Gln Ala Leu Leu Glu Glu
                80                  85                  90

Gln Asn Leu Ser Val Ala Glu Gly Pro Asn Tyr Leu Thr Ala Cys
                95                 100                 105

Ala Gly Pro Pro Ser Arg Pro Gln Arg Pro Phe Cys Ala Val Cys
               110                 115                 120

Gly Phe Pro Ser Pro Tyr Thr Cys Val Ser Cys Gly Ala Arg Tyr
               125                 130                 135

Cys Thr Val Arg Cys Leu Gly Thr His Gln Glu Thr Arg Cys Leu
               140                 145                 150

Lys Trp Thr Val
          154

<210> SEQ ID NO 2
<211> LENGTH: 735
<212> TYPE: DNA
<213> ORGANISM: Homo sapiens
<220> FEATURE:
<223> OTHER INFORMATION: cDNA sequence of TADG5 gene isolated from a
      cDNA ovarian library

<400> SEQUENCE: 2
ggggccccta ctaaagcctt ggggttagta cgcgtgcgca gcagtttctt           50
ccgacagttg tgttgtgcca atggtggaga agaaaacttc ggttcgctcc          100
caggaccccg ggcagcggcg ggtgctggac cgggctgccc ggcagcgtcg          150
catcaaccgg cagctggagg ccctggagaa tgacaacttc caggatgacc          200
cccacgcggg actccctcag ctcggcaaga gactgcctca gtttgatgac          250

```
gatgcggaca ctggaaagaa aaagaagaaa acccgaggtg atcattttaa           300
acttcgcttc cgaaaaaact ttcaggccct gttggaggag cagaacttga           350
gtgtggccga gggccctaac tacctgacgg cctgtgcggg accccatcg            400 cggccccagc gccccttctg tgctgtctgt ggcttcccat cccccctacac          450 ctgtgtcagc tgcggtgccc ggtactgcac tgtgcgctgt ctggggaccc           500
accaggagac caggtgtctg aagtggactg tgtgagcctg gcattccca            550 gagaggaagg gccgctgtgc actgcccggc cttcagaaag acagaatttc           600
atcacccaat gcaggggag catttcctcg tccaagggag agcctcactc            650
ctgggaactg tctggcaggt aggctgggcc ccccagtgct gttagattaa           700
aaatcctcgt gctggaaaaa aaaaaaaaaa aaaaa                           735
```

```
<210> SEQ ID NO 3
<211> LENGTH: 15
<212> TYPE: DNA
<213> ORGANISM: Artificial Sequence
<220> FEATURE:
<223> OTHER INFORMATION: nucleotide sequence of clone 12 isolated using
      the CASTing approach

<400> SEQUENCE: 3
ctggcaatct gacta                                                 15

<210> SEQ ID NO 4
<211> LENGTH: 15
<212> TYPE: DNA
<213> ORGANISM: Artificial Sequence
<220> FEATURE:
<223> OTHER INFORMATION: nucleotide sequence of clone 14 isolated using
      the CASTing approach

<400> SEQUENCE: 4
ctggcaatct gacta                                                 15

<210> SEQ ID NO 5
<211> LENGTH: 15
<212> TYPE: DNA
<213> ORGANISM: Artificial Sequence
<220> FEATURE:
<223> OTHER INFORMATION: nucleotide sequence of clone 18 isolated using
      the CASTing approach

<400> SEQUENCE: 5
tagtcggatg gtatg                                                 15

<210> SEQ ID NO 6
<211> LENGTH: 15
<212> TYPE: DNA
<213> ORGANISM: Artificial Sequence
<220> FEATURE:
<223> OTHER INFORMATION: nucleotide sequence of clone 13 isolated using
      the CASTing approach

<400> SEQUENCE: 6 aagaggggt tgagg                                                  15

<210> SEQ ID NO 7
<211> LENGTH: 15
<212> TYPE: DNA
<213> ORGANISM: Artificial Sequence
<220> FEATURE:
```

```
<223> OTHER INFORMATION: nucleotide sequence of clone 16 isolated using
      the CASTing approach

<400> SEQUENCE: 7
taactggggt tagat                                                    15

<210> SEQ ID NO 8
<211> LENGTH: 15
<212> TYPE: DNA
<213> ORGANISM: Artificial Sequence
<220> FEATURE:
<223> OTHER INFORMATION: nucleotide sequence of clone 15 isolated using
      the CASTing approach

<400> SEQUENCE: 8
tttgtgggtg ggggg                                                    15

<210> SEQ ID NO 9
<211> LENGTH: 15
<212> TYPE: DNA
<213> ORGANISM: Artificial Sequence
<220> FEATURE:
<223> OTHER INFORMATION: nucleotide sequence of clone 17 isolated using
      the CASTing approach

<400> SEQUENCE: 9
gggtgggggg gtggc                                                    15

<210> SEQ ID NO 10
<211> LENGTH: 15
<212> TYPE: DNA
<213> ORGANISM: Artificial Sequence
<220> FEATURE:
<223> OTHER INFORMATION: nucleotide sequence of clone 22 isolated using
      the CASTing approach

<400> SEQUENCE: 10 tgggggagc gaata                                                     15

<210> SEQ ID NO 11
<211> LENGTH: 15
<212> TYPE: DNA
<213> ORGANISM: Artificial Sequence
<220> FEATURE:
<223> OTHER INFORMATION: nucleotide sequence of clone 23 isolated using
      the CASTing approach

<400> SEQUENCE: 11
tgaatcatgg gggac                                                    15

<210> SEQ ID NO 12
<211> LENGTH: 15
<212> TYPE: DNA
<213> ORGANISM: Artificial Sequence
<220> FEATURE:
<223> OTHER INFORMATION: nucleotide sequence of clone 19 isolated using
      the CASTing approach

<400> SEQUENCE: 12
gaaaggttaa gcgac                                                    15

<210> SEQ ID NO 13
<211> LENGTH: 15
<212> TYPE: DNA
<213> ORGANISM: Artificial Sequence
<220> FEATURE:
<223> OTHER INFORMATION: nucleotide sequence of clone 20 isolated using
``` the CASTing approach

<400> SEQUENCE: 13
attggttaag gcgac                                                                                           15

<210> SEQ ID NO 14
<211> LENGTH: 12
<212> TYPE: PRT
<213> ORGANISM: Artificial Sequence
<220> FEATURE:
<221> NAME/KEY: Peptide
<223> OTHER INFORMATION: amino acid sequence of a peptide used to
      produce polyclonal antibodies which bind the TADG5 protein

<400> SEQUENCE: 14

Arg Val Leu Asp Arg Ala Ala Arg Gln Arg Arg Ile
              5                  10

<210> SEQ ID NO 15
<211> LENGTH: 12
<212> TYPE: PRT
<213> ORGANISM: Artificial Sequence
<220> FEATURE:
<221> NAME/KEY: Peptide
<223> OTHER INFORMATION: amino acid sequence of a peptide used to
      produce polyclonal antibodies which bind the TADG5 protein

<400> SEQUENCE: 15

Tyr Cys Thr Val Arg Cys Leu Gly Thr His Gln Glu
              5                  10

<210> SEQ ID NO 16
<211> LENGTH: 697
<212> TYPE: DNA
<213> ORGANISM: Homo sapiens
<220> FEATURE:
<221> NAME/KEY: mat_peptide
<222> LOCATION: 5, 82, 150, 151, 203, 208, 211, 565, 566, 574, 582
<223> OTHER INFORMATION: partial cDNA sequence of human putative cyclin
      G1 interacting protein HSU618, n = unknown

<400> SEQUENCE: 16
cggcncgagc tcgtgccgct tcggttcgct cccaggaccc cgggcagcgg         50
ctggtgctgg accgggctgc ccggctgcgt cncatcaacc ggcagctgga        100
ggccctggag aatgactact ttcaggatga ctcccatcgg gactccctcn        150
nctcggcaag agactgcctc agtttgatta ctattcggac actggaaaga        200
aanagaanaa naatacccga ggtgatcatt taaacttcg cttccgaaaa         250 aactttcagg ccctgttgga ggagcagaac ttgagtgtgg ccgagggcct        300
aactacctga cggcctgtgc gggaccccca tcgcggcccc agcgccccctt       350 ctgtgctgtc tgtggcttcc catcccccta cacctgtgtc agctgcggtg        400
cccggtactg cactgtgcgc tgtctgggga cccaccagga gaccaggtgt        450
ctgaagtgga ctgtgtgagc ctgggcattc agagaggaa gggccgctgt         500 ccactgcccg gccttcagaa agacagaatt gcatcaccca atgcaggggg        550
agcttttcct ggacnnaggg aggngccgct cnttcaccaa acaaaactgt        600
gtctcatctg ccaggaaaga ccagcttcac tcctgggaac tgtctggcag        650
gtaggctggg cccccagtg ctgttagaat aaaaagcctc gtgccgg            697

<210> SEQ ID NO 17

```
<211> LENGTH: 55
<212> TYPE: PRT
<213> ORGANISM: unknown
<220> FEATURE:
<221> NAME/KEY: Domain
<223> OTHER INFORMATION: amino acid sequence of C-Fgr SH3 domain

<400> SEQUENCE: 17

Ala Leu Tyr Asp Tyr Glu Ala Arg Thr Glu Asp Asp Leu Thr Phe
                 5                  10                  15

Thr Lys Gly Glu Lys Phe His Ile Leu Asn Asn Thr Glu Gly Asp
                20                  25                  30

Trp Trp Glu Ala Arg Ser Leu Ser Ser Gly Lys Thr Gly Cys Ile
                35                  40                  45

Pro Ser Asn Tyr Val Ala Pro Val Asp Ser
                50                  55

<210> SEQ ID NO 18
<211> LENGTH: 54
<212> TYPE: PRT
<213> ORGANISM: unknown
<220> FEATURE:
<221> NAME/KEY: Domain
<223> OTHER INFORMATION: amino acid sequence of C-Tkl SH3 domain

<400> SEQUENCE: 18

Ala Leu Tyr Asp Tyr Glu Pro Thr His Asp Gly Asp Leu Gly Leu
                 5                  10                  15

Lys Gln Gly Glu Lys Leu Arg Val Leu Glu Glu Ser Gly Glu Trp
                20                  25                  30

Trp Arg Ala Gln Ser Leu Thr Thr Gly Gln Glu Gly Leu Ile Pro
                35                  40                  45

His Asn Phe Val Ala Met Val Asn Ser
                50

<210> SEQ ID NO 19
<211> LENGTH: 54
<212> TYPE: PRT
<213> ORGANISM: unknown
<220> FEATURE:
<221> NAME/KEY: Domain
<223> OTHER INFORMATION: amino acid sequence of C-Abl SH3 domain

<400> SEQUENCE: 19

Ala Leu Tyr Asp Phe Val Ala Ser Gly Asp Asn Thr Leu Ser Ile
                 5                  10                  15

Thr Lys Gly Glu Lys Leu Arg Val Leu Gly Tyr Asn His Asn Gly
                20                  25                  30

Glu Trp Cys Glu Ala Gln Thr Lys Asn Gly Gln Gly Trp Val Pro
                35                  40                  45

Ser Asn Tyr Ile Thr Pro Val Asn Ser
                50                  54

<210> SEQ ID NO 20
<211> LENGTH: 53
<212> TYPE: PRT
<213> ORGANISM: unknown
<220> FEATURE:
<221> NAME/KEY: Domain
<223> OTHER INFORMATION: amino acid sequence of Ncf2a SH3 domain

<400> SEQUENCE: 20

Val Leu Phe Gly Phe Val Pro Glu Thr Lys Glu Glu Leu Gln Val
```

```
                    5                   10                  15
Met Pro Gly Asn Ile Val Phe Val Leu Lys Lys Gly Asn Asp Asn
                    20                  25                  30

Trp Ala Thr Val Met Phe Asn Gly Gln Lys Gly Leu Val Pro Cys
                    35                  40                  45

Asn Tyr Leu Glu Pro Val Glu Leu
                    50              53

<210> SEQ ID NO 21
<211> LENGTH: 54
<212> TYPE: PRT
<213> ORGANISM: unknown
<220> FEATURE:
<221> NAME/KEY: Domain
<223> OTHER INFORMATION: amino acid sequence of Vav SH3 domain

<400> SEQUENCE: 21

Ala Arg Tyr Asp Phe Cys Ala Arg Asp Arg Ser Glu Leu Ser Leu
                    5                   10                  15

Lys Glu Gly Asp Ile Ile Lys Ile Leu Asn Lys Lys Gly Gln Gln
                    20                  25                  30

Gly Trp Trp Arg Gly Glu Ile Tyr Gly Arg Val Gly Trp Phe Pro
                    35                  40                  45

Ala Asn Tyr Val Glu Glu Asp Tyr Ser
                    50              54

<210> SEQ ID NO 22
<211> LENGTH: 52
<212> TYPE: PRT
<213> ORGANISM: Homo sapiens
<220> FEATURE:
<221> NAME/KEY: Domain
<222> LOCATION: 80...131
<223> OTHER INFORMATION: amino acid sequence of TADG5 SH3 domain

<400> SEQUENCE: 22

Phe Arg Lys Asn Phe Gln Ala Leu Leu Glu Glu Gln Asn Leu Ser
                    5                   10                  15

Val Ala Glu Gly Pro Asn Tyr Leu Thr Ala Cys Ala Gly Pro Pro
                    20                  25                  30

Ser Arg Pro Gln Arg Pro Phe Cys Ala Val Cys Gly Phe Pro Ser
                    35                  40                  45

Pro Tyr Thr Cys Val Ser Cys
                    50              52

<210> SEQ ID NO 23
<211> LENGTH: 47
<212> TYPE: PRT
<213> ORGANISM: Artificial Sequence
<220> FEATURE:
<221> NAME/KEY: Domain
<222> LOCATION: 81...127
<223> OTHER INFORMATION: amino acid sequence of most of the TADG5 SH3
      domain

<400> SEQUENCE: 23

Arg Lys Asn Phe Gln Ala Leu Leu Glu Glu Gln Asn Leu Ser Val
                    5                   10                  15

Ala Glu Gly Pro Asn Tyr Leu Thr Ala Cys Ala Gly Pro Pro Ser
                    20                  25                  30

Arg Pro Gln Arg Pro Phe Cys Ala Val Cys Gly Phe Pro Ser Pro
                    35                  40                  45
```

Tyr Thr
    47

<210> SEQ ID NO 24
<211> LENGTH: 48
<212> TYPE: PRT
<213> ORGANISM: unknown
<220> FEATURE:
<221> NAME/KEY: Domain
<222> LOCATION: 2...49
<223> OTHER INFORMATION: amino acid sequence of Vav SH3 domain at
      position 2 through position 49 of SEQ ID No. 21

<400> SEQUENCE: 24

Arg Tyr Asp Phe Cys Ala Arg Asp Arg Ser Glu Leu Ser Leu Lys
                 5                  10                  15

Glu Gly Asp Ile Ile Lys Ile Leu Asn Lys Lys Gly Gln Gln Gly
                20                  25                  30

Trp Trp Arg Gly Glu Ile Tyr Gly Arg Val Gly Trp Phe Pro Ala
                35                  40                  45

Asn Tyr Val
        48

<210> SEQ ID NO 25
<211> LENGTH: 28
<212> TYPE: PRT
<213> ORGANISM: Homo sapiens
<220> FEATURE:
<221> NAME/KEY: Domain
<222> LOCATION: 124...151
<223> OTHER INFORMATION: amino acid sequence of TADG5 at position 124
      through position 151, which is homologous to zinc
      finger II of TFIII

<400> SEQUENCE: 25

Ser Pro Tyr Thr Cys Val Ser Cys Gly Ala Arg Tyr Cys Thr Val
                 5                  10                  15

Arg Cys Leu Gly Thr His Gln Glu Thr Arg Cys Leu Lys
                20                  25          28

<210> SEQ ID NO 26
<211> LENGTH: 28
<212> TYPE: PRT
<213> ORGANISM: unknown
<220> FEATURE:
<221> NAME/KEY: Domain
<222> LOCATION: 104...131
<223> OTHER INFORMATION: amino acid sequence of zinc finger II domain of
      TFIII

<400> SEQUENCE: 26

Asn Pro Tyr Arg Cys Ser Gln Cys Gly Lys Ala Phe Arg Arg Thr
                 5                  10                  15

Ser Asp Leu Ser Ser His Arg Arg Thr Gln Cys Ile Lys
                20                  25          28

<210> SEQ ID NO 27
<211> LENGTH: 23
<212> TYPE: PRT
<213> ORGANISM: Homo sapiens
<220> FEATURE:
<221> NAME/KEY: Domain
<222> LOCATION: 111...133
<223> OTHER INFORMATION: amino acid sequence of TADG5 at position 111
      through position 133, which is homologous to zinc
      finger domain of a yeast protein

<400> SEQUENCE: 27

Arg Pro Gln Arg Pro Phe Cys Ala Val Cys Gly Phe Pro Ser Pro
                5                   10                  15

Tyr Thr Cys Val Ser Cys Gly Ala
                20          23

<210> SEQ ID NO 28
<211> LENGTH: 23
<212> TYPE: PRT
<213> ORGANISM: yeast
<220> FEATURE:
<221> NAME/KEY: Domain
<222> LOCATION: 370...392
<223> OTHER INFORMATION: amino acid sequence of zinc finger domain of a
      yeast protein

<400> SEQUENCE: 28

Arg Pro Gln Asp Ser Tyr Cys Pro His Cys Gly Tyr Tyr Gln Tyr
                5                   10                  15

Val Glu Cys Val Ser Cys His Ala
                20          23

<210> SEQ ID NO 29
<211> LENGTH: 29
<212> TYPE: PRT
<213> ORGANISM: Homo sapiens
<220> FEATURE:
<221> NAME/KEY: Domain
<222> LOCATION: 121...149
<223> OTHER INFORMATION: amino acid sequence of TADG5 at position 121
      through position 149, which is homologous to zinc
      finger domain of a yeast protein

<400> SEQUENCE: 29

Gly Phe Pro Ser Pro Tyr Thr Cys Val Ser Cys Gly Ala Arg Tyr
                5                   10                  15

Cys Thr Val Arg Cys Leu Gly Thr His Gln Glu Thr Arg Cys
                20                  25              29

<210> SEQ ID NO 30
<211> LENGTH: 29
<212> TYPE: PRT
<213> ORGANISM: yeast
<220> FEATURE:
<221> NAME/KEY: Domain
<222> LOCATION: 249...277
<223> OTHER INFORMATION: amino acid sequence of zinc finger domain of a
      yeast protein

<400> SEQUENCE: 30

Gly Tyr Asp Ser Ile Ser Ser Cys Val Asn Cys Gly Asn Lys Ile
                5                   10                  15

Cys Ser Val Ser Cys Phe Lys Leu His Asn Glu Thr Arg Cys
                20                  25              29

<210> SEQ ID NO 31
<211> LENGTH: 679
<212> TYPE: DNA
<213> ORGANISM: Homo sapiens
<220> FEATURE:
<221> NAME/KEY: mat_peptide
<222> LOCATION: 19...697
<223> OTHER INFORMATION: partial cDNA sequence of human putative cyclin
      G1 interacting protein HSU618, "n" at nt 64, 132, 133,
      185, 190, 193, 547, 548, 556, 564 and 623 is
      unknown

<400> SEQUENCE: 31

```
cttcggttcg ctcccaggac cccgggcagc ggctggtgct ggaccgggct      50
gcccggctgc gtcncatcaa ccggcagctg gaggccctgg agaatgacta     100
ctttcaggat gactcccatc gggactccct cnnctcggca agagactgcc     150
tcagtttgat tactattcgg acactggaaa gaaanagaan aanaataccc     200
gaggtgatca ttttaaactt cgcttccgaa aaaactttca ggccctgttg     250
gaggagcaga acttgagtgt ggccgagggc ctaactacct gacggcctgt     300
gcgggacccc catcgcggcc ccagcgcccc ttctgtgctg tctgtggctt     350
cccatccccc tacacctgtg tcagctgcgg tgcccggtac tgcactgtgc     400
gctgtctggg gacccaccag gagaccaggt gtctgaagtg ccactgcccg     450
gactgtgtga gcctgggcat tccagagagg aagggccgct gtgccttcag     500
aaagacagaa ttgcatcacc caatgcaggg ggagcttttc ctggacnnag     550
ggaggngccg ctcnttcacc aaacaaaact gtgtctcatc tgccaggaaa     600
gaccagcttc actcctggga acngtctggc aggtaggctg ggcccccccag    650
tgctgttaga ataaaaagcc tcgtgccgg                            679
```

<210> SEQ ID NO 32
<211> LENGTH: 629
<212> TYPE: DNA
<213> ORGANISM: Homo sapiens
<220> FEATURE:
<221> NAME/KEY: mat_peptide
<222> LOCATION: 87...715
<223> OTHER INFORMATION: cDNA sequence of TADG5 gene at position 87 through position 715

<400> SEQUENCE: 32

```
cttcggttcg ctcccaggac cccgggcagc ggcgggtgct ggaccgggct      50
gcccggcagc gtcgcatcaa ccggcagctg gaggccctgg agaatgacaa     100
cttccaggat gaccccacg cgggactccc tcagctcggc aagagactgc      150
ctcagtttga tgacgatgcg gacactggaa agaaaaagaa gaaaacccga     200
ggtgatcatt ttaaacttcg cttccgaaaa actttcagg ccctgttgga      250
ggagcagaac ttgagtgtgg ccgagggccc taactacctg acggcctgtg    300
cgggaccccc atcgcggccc cagcgccct tctgtgctgt ctgtggcttc     350
ccatccccct acacctgtgt cagctgcggt gcccggtact gcactgtgcg    400
ctgtctgggg acccaccagg agaccaggtg tctgaagtgg actgtgtgag    450
cctgggcatt cccagagagg aagggccgct gtgcactgcc cggccttcag    500
aaagacagaa tttcatcacc caatgcaggg ggagcatttc ctcgtccaag    550
ggagagcctc actcctggga actgtctggc aggtaggctg ggcccccccag   600
tgctgttaga ttaaaaatcc tcgtgctgg                           629
```